United States Patent
Clark et al.

(10) Patent No.: US 10,506,936 B2
(45) Date of Patent: *Dec. 17, 2019

(54) APPARATUSES AND METHODS FOR NEUROLOGIC STATUS EVALUATION USING ELECTROMAGNETIC SIGNALS

(71) Applicant: University Of Cincinnati, Cincinnati, OH (US)

(72) Inventors: Joseph Floyd Clark, Cincinnati, OH (US); Matthew L. Flaherty, Cincinnati, OH (US); George Shaw, Cincinnati, OH (US); Opeolu Adeoye, Cincinnati, OH (US)

(73) Assignee: University Of Cincinnati, Cincinnati, OH (US)

( * ) Notice: Subject to any disclaimer, the term of this patent is extended or adjusted under 35 U.S.C. 154(b) by 456 days.

This patent is subject to a terminal disclaimer.

(21) Appl. No.: 15/174,308

(22) Filed: Jun. 6, 2016

(65) Prior Publication Data

US 2016/0278653 A1    Sep. 29, 2016

Related U.S. Application Data

(63) Continuation of application No. 13/977,689, filed as application No. PCT/US2011/068095 on Dec. 30, 2011, now Pat. No. 9,357,970.

(Continued)

(51) Int. Cl.
*A61B 5/05* (2006.01)
*A61B 5/04* (2006.01)
(Continued)

(52) U.S. Cl.
CPC ........ *A61B 5/04008* (2013.01); *A61B 5/0042* (2013.01); *A61B 5/0075* (2013.01);
(Continued)

(58) Field of Classification Search
None
See application file for complete search history.

(56) References Cited

U.S. PATENT DOCUMENTS 3,951,134 A * 4/1976 Malech ............... A61B 5/0006
600/544
5,573,012 A   11/1996 McEwan
(Continued)

FOREIGN PATENT DOCUMENTS

WO   2006135520 A1   12/2006

OTHER PUBLICATIONS

NEC, preliminary production information. Compact disc digital serve/data processor with on-chip RF amplifier.
(Continued)

*Primary Examiner* — Joel F Brutus
(74) *Attorney, Agent, or Firm* — Wood Herron & Evans LLP

(57) ABSTRACT

In one embodiment, a neurological status evaluation apparatus includes a signal generator configured to generate an electromagnetic signal at one or more frequencies, a transmitting antenna coupled to the signal generator and configured to transmit the electromagnetic signal, and a receiving antenna positioned proximate to the transmitting antenna such that an evaluation space is defined between the transmitting antenna and the receiving antenna. The biological tissue under evaluation does not contact the transmitting antenna or the receiving antenna. The receiving antenna receives a modulated electromagnetic signal after propagating through the biological tissue under evaluation. The neurological status evaluation apparatus further includes a spectrum analyzer coupled to the receiving antenna, wherein the spectrum analyzer receives and samples the modulated electromagnetic signal. A computing device is coupled to the spectrum analyzer, calculates an evaluation, and provides a (Continued)

neurological status indicator of the biological tissue under evaluation based on the evaluation parameter.

20 Claims, 11 Drawing Sheets

Related U.S. Application Data

(60) Provisional application No. 61/428,407, filed on Dec. 30, 2010.

(51) Int. Cl.
  *A61B 5/00* (2006.01)
  *A61B 5/02* (2006.01)

(52) U.S. Cl.
  CPC ...... *A61B 5/02042* (2013.01); *A61B 5/04001* (2013.01); *A61B 5/4064* (2013.01); *A61B 5/4094* (2013.01); *A61B 5/4878* (2013.01); *A61B 5/6803* (2013.01); *A61B 5/7225* (2013.01); *A61B 5/7257* (2013.01); *A61B 5/7282* (2013.01); *A61B 5/742* (2013.01); *A61B 5/746* (2013.01); *A61B 2562/0223* (2013.01); *A61B 2576/026* (2013.01)

(56) References Cited

U.S. PATENT DOCUMENTS

| | | | |
|---|---|---|---|
| 6,026,173 A | 2/2000 | Svenson et al. | |
| 6,064,903 A | 5/2000 | Riechers et al. | |
| 6,332,087 B1 | 12/2001 | Svenson et al. | |
| 7,239,151 B2 | 7/2007 | Bailey et al. | |
| 8,361,391 B2 | 1/2013 | Rubinsky et al. | |
| 8,724,864 B2 | 5/2014 | Persson et al. | |
| 2003/0018244 A1 | 1/2003 | Haddad et al. | |
| 2003/0036674 A1* | 2/2003 | Bouton | A61B 5/05 600/12 |
| 2007/0106172 A1 | 5/2007 | Abreu | |
| 2008/0200802 A1* | 8/2008 | Bhavaraju | A61B 5/05 600/426 |
| 2009/0281414 A1 | 11/2009 | Feldman et al. | |
| 2010/0041962 A1 | 2/2010 | Causevic et al. | |
| 2010/0069744 A1 | 3/2010 | Simpkin | |
| 2010/0217099 A1 | 8/2010 | LeBoeuf et al. | |

OTHER PUBLICATIONS

European Patent Office, Extended Supplemental European Search Report issued in corresponding EP Application No. 11853463.5, dated Nov. 25, 2015, 9 pages.

Andreas Fhager et al, A microwave measurement system for stroke detection, Antennas and Propagation Conference (LAPC), 2011 Loughborough, IEEE, Nov. 14, 2011, pp. 1-2.

Fhager, A, et al., Reconstruction Quality and Spectral Content of an Electromagnetic Time-Domain Inversion algorithm, IEEE Transactions on Biomedical Engineering, vol. 53, No. 1, Aug. 1, 2006, pp. 1594-1604.

European Patent Office, Extended European Search Report issued in corresponding European Patent Application No. 18151801.0, dated Aug. 21, 2018, 9 pages.

\* cited by examiner

APPARATUSES AND METHODS FOR NEUROLOGIC STATUS EVALUATION USING ELECTROMAGNETIC SIGNALS

This application is a continuation of pending U.S. application Ser. No. 13/977,689 filed May 12, 2014, entitled "APPARATUSES AND METHODS FOR NEUROLOGICAL STATUS EVALUATION USING ELECTROMAGNETIC SIGNALS," which is the U.S. National Phase Application of PCT Application No. PCT/US2011/068095 filed Dec. 30, 2011, entitled "APPARATUSES AND METHODS FOR NEUROLOGICAL STATUS EVALUATION USING ELECTROMAGNETIC SIGNALS," which claims priority to U.S. Provisional Application Ser. No. 61/428,407 filed on Dec. 30, 2010, and entitled "SENSOR EVALUATION OF NEUROLOGIC STATUS IN EMERGENCIES (SENSE) DEVICE," which applications are incorporated by reference in their entirety.

BACKGROUND

There is a clinical need for non-invasive neurologic monitoring in the intensive care unit (ICU), Emergency Department (ED), operating room (OR), battlefield, and pre-hospital settings. Currently, clinicians can assess the neurologic status of a patient by either performing a clinical neurological exam or through imaging of the central nervous system (CNS) using computed tomography (CT) or magnetic resonance imaging (MRI). Further, there exists a need for a non-invasive test of neurologic status that can alert the treating clinician to significant changes in the CNS status of the patient, such as hemorrhage, increase in intracranial pressure, cerebral edema or seizure.

Detecting bleeding in the brain from trauma or stroke is an important piece of diagnostic information. The sooner this information can be obtained by emergency medical technicians, paramedics, emergency room physicians, or intensive care physicians, the better the care for the head-injured patient. For ambulance personnel, knowing if a patient has a brain bleed will aid greatly in directing a patient's transport to a hospital with a trauma team and/or brain surgeon.

Currently, there are no active monitoring devices used for monitoring the brain changes transcranially. Current state-of-the-art and cutting edge technologies focus on highly specialized techniques such as electroencephalography (EEG), magnetoencephalography (MEG) and electrical impedance tomograpy (EIT). As described in more detail below, embodiments of the present disclosure measure and analyze changes made to the active signal resulting from propagation through the biological tissue, which is a new approach that has not previously been explored in the art.

Accordingly, a need exists for non-invasive neurologic monitoring of biological tissue, such as a human brain, that does not require interpretation by a trained technician, and may be deployed in a wide variety of settings, such as emergency rooms, ambulance vehicles, health care facilities, nursing care facilities, and the like.

SUMMARY

In one embodiment, a neurological status evaluation apparatus includes a signal generator configured to generate an electromagnetic signal at one or more frequencies, a transmitting antenna coupled to the signal generator, wherein the transmitting antenna is configured to transmit the electromagnetic signal, and a receiving antenna positioned proximate to the transmitting antenna such that an evaluation space is defined between the transmitting antenna and the receiving antenna. The evaluation space is configured to receive a biological tissue under evaluation such that the biological tissue under evaluation does not contact the transmitting antenna nor the receiving antenna. The receiving antenna receives a modulated electromagnetic signal after propagating through the biological tissue under evaluation. The neurological status evaluation apparatus further includes a spectrum analyzer coupled to the receiving antenna, wherein the spectrum analyzer receives the modulated electromagnetic signal and samples spectrum data of the modulated electromagnetic signal, and a computing device coupled to the spectrum analyzer. The computing device calculates an evaluation parameter based at least in part on the sampled spectrum data of the modulated electromagnetic signal, and provides a neurological status indicator of the biological tissue under evaluation based at least in part on the evaluation parameter.

In another embodiment, a transcranial neurological evaluation apparatus includes a signal configured to generate an electromagnetic signal at one more frequencies, a headband portion configured to be positioned about a human head, and a plurality of transceiver devices positioned on the headband portion. Each individual transceiver device of the plurality of transceiver devices includes a transmitting antenna coupled to the signal generator, and a receiving antenna. The transmitting antenna is configured to transmit the electromagnetic signal. The transmitting antenna and the receiving antenna do not make electrical contact with the human head, and the receiving antenna receives a modulated electromagnetic signal after propagating through a brain of the human head. The transcranial neurological evaluation apparatus further includes a spectrum analyzer coupled to the receiving antenna of each transceiver device of the plurality of transceiver devices, and a computing device coupled to the spectrum analyzer. The spectrum analyzer receives the modulated electromagnetic signal and samples spectrum data of the modulated electromagnetic signal. The computing device calculates an evaluation parameter for each transceiver device based at least in part on the sampled spectrum data of each modulated electromagnetic signal, and provides a neurological status indicator of the brain based at least in part on one or more of the evaluation parameters.

In yet another embodiment, a method of evaluating a status of biological tissue includes transmitting an electromagnetic signal into a biological tissue under evaluation, and receiving a modulated electromagnetic signal emitted by the biological tissue under evaluation, wherein the electromagnetic signal is transmitted from a transmitting antenna that is not in electrical contact with the biological tissue under evaluation, and the modulated electromagnetic signal is received by a receiving antenna that is not in electrical contact with the biological tissue under evaluation. The method further includes sampling spectrum data of the modulated electromagnetic signal, and calculating an evaluation parameter based at least in part on the sampled spectrum data of the modulated electromagnetic signal, wherein the evaluation parameter corresponds to a dielectric property of the biological tissue under evaluation. The method additionally includes providing a neurological status indicator of the biological tissue under evaluation based at least in part on the evaluation parameter.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
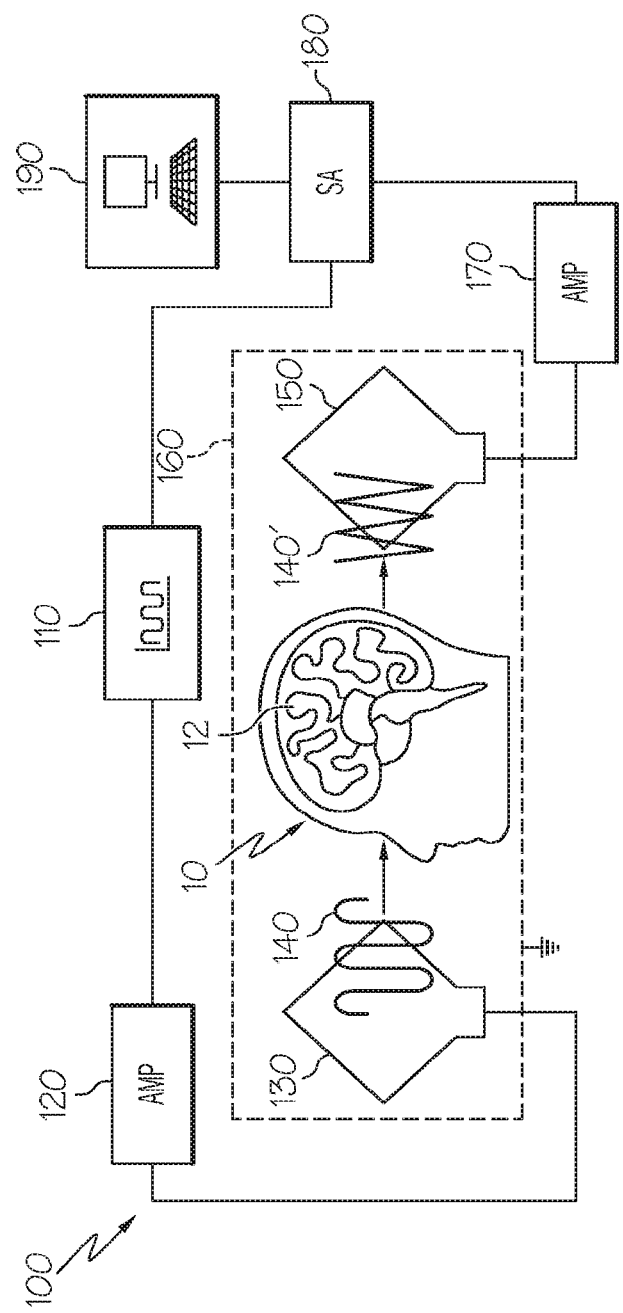
FIG. 1 depicts a schematic illustration of a neurological evaluation apparatus according to one or more embodiments shown and described herein.

Embodiments of the present disclosure are directed to apparatuses and methods for detecting and evaluating the neurological status of biological tissue under evaluation, such as the human brain. The embodiments described herein provide an indicator of changes in neurologic function of the biological tissue that is under evaluation. Generally, embodiments subject the biological tissue to a non-invasive, tailored electromagnetic signal. The electromagnetic signal is input into the biological tissue by a transmitting antenna, wherein it then interacts with the biological tissue. The resulting modulated electromagnetic signal that is emitted by the biological tissue is then received by a receiving antenna. The electromagnetic signal transmitted by the transmitting antenna may be altered by the electrical properties of the biological tissue (e.g., resistance, conductance, and dielectric properties), and the altered/modulated electromagnetic signal having passed through the biological tissue is received by the receiving antenna. Modulation of the electromagnetic signal within the biological tissue can be caused by (1) alterations in the electrical properties of the central nervous system, such as the permittivity ε or conductivity σ, and (2) by changes in the central nervous system geometry such as an intracranial hemorrhage (ICH). Embodiments utilize different frequencies of electromagnetic radiation to allow detection of differing intracranial pathologies. It is noted that although embodiments of the present disclosure are described in the context of biological tissue in the form of the brain, embodiments are not limited thereto.

Substantial changes in the electromagnetic signal may result in an alarm to alert the treating clinician that further evaluation of the patient is required. The resulting changes induced by the electromagnetic signal's interaction with the biological tissue under evaluation is measured. The changes of the modulated electromagnetic signal may be indicative of blood or bleeding (e.g., subdural or epidural hematoma), seizures, and/or edema in the brain. The changes in the modulated electromagnetic signal may be brought to the attention of the treating clinician such that a decision may be made for further interventions.

Embodiments of the present disclosure may be useful in critical care monitoring settings including, but not limited to, the intensive care unit (ICU) or neurosurgical intensive care unit (NICU) of hospitals. These patients in these care units are often comatose or sedated and paralyzed, thus rendering ongoing neurological evaluation problematic.

Further, the trans-cranial, trans-dermal devices described herein may detect small volumes of hemorrhage (e.g., as small as 3 ml) in the brain after a traumatic brain injury (TBI). Early evaluation and continued monitoring of traumatic brain injuries may decrease missed opportunities for treatment in both the military and civilian populations. The natural history of TBI is such that an initial small amount of bleeding may not result in gross neurological dysfunction. However, ongoing bleeding and cerebral edema may result in sudden catastrophic neurological decline. In moderate or severe TBI, patients often experience progressive bleeding or edema formation. Currently, there is no established continuous monitor that may be used to detect ongoing intracranial bleeding and/or progression of cerebral edema. As such, clinical practice is reactionary; acting only when clinical symptoms manifest. Sufficient neurological decline must occur, with the consequent adverse effect on outcome, prior to medical and/or surgical intervention.

Accordingly, embodiments of the present disclosure are directed to non-invasive, field deployable, continuous brain monitors that detect ongoing intracranial bleeding and cerebral edema that may minimize missed opportunities for treatment of TBI.

Referring now to FIG. 1, a schematic illustration of a biological status evaluation apparatus 100 to evaluate biological tissue 12 according to one embodiment is provided. The biological status evaluation apparatus depicted in FIG. 1 is configured as a neurological status evaluation apparatus to detect neurological events or conditions within the brain. The neurological status evaluation apparatus 100 generally comprises a signal generator 110, a first amplifier 120, a transmitting antenna 130, a receiving antenna 150, a second amplifier 170, a spectrum analyzer 180, and a computing device 190. The neurological status evaluation apparatus 100 depicted in FIG. 1 further comprises an optional Faraday cage 160 that maintains the transmitting antenna 130, the biological tissue under evaluation 12, and the receiving antenna 150.

The signal generator 110 may be configured as any signal generator device or circuit capable of generating the desired electromagnetic signal 140 at the desired frequency and amplitude. The properties of the electromagnetic signal 140 are described in more detail below, and may depend on the particular application in which the neurological status evaluation apparatus is to be utilized. In one embodiment, the signal generator 110 is capable of producing an electromagnetic signal at a frequency within the range of about 400 MHz to about 2 GHz. The first amplifier 120 is provided to amplify the signal produced by the signal generator 110 to a desired power level. The first amplifier 120 may be included in the signal generator 110 as a single component, in some embodiments.

The transmitting antenna 130 is electrically coupled to either the first amplifier 120 or the signal generator 110 such that it receives the electromagnetic signal 140 for transmission toward and through the biological tissue under evaluation 12. In one embodiment, the transmitting antenna 130 is a directional antenna that is configured to directionally propagate the electromagnetic signal 140 toward the biological tissue under evaluation 12.

The transmitting antenna 130 and the receiving antenna 150 are arranged to define an evaluation space for the positioning of the biological tissue under evaluation 12. The biological tissue under evaluation 12 illustrated in FIG. 1 is a brain of a human head 10. Unlike conventional devices that provide for passive measurements of the signals produced by the brain, the transmitting antenna 130 and the receiving antenna 150 are arranged such that transmitting antenna 130 and the receiving antenna 150 are not in electrical contact with the subject biological tissue that is positioned within the evaluation space. This allows for free propagation of the electromagnetic signal 140 through the biological tissue under evaluation 12. As stated above, the transmitting antenna 130, the biological tissue under evaluation 12, and the receiving antenna 150 may be positioned within an optional Faraday cage to reduce external noise to and from the environment in which the neurological status evaluation apparatus 100 is operating.

As shown in FIG. 1 and described in more detail below, the electromagnetic signal 140 enters the biological tissue under evaluation 12 where it is modulated by the biological tissue's dielectric properties such that a modulated electromagnetic signal 140' is received by the receiving antenna 150. The receiving antenna 150 may be electrically coupled to the second amplifier 170 such that the modulated electromagnetic signal 140' is passed to the second amplifier 170 for amplification. The amplified electromagnetic signal is then provided to a spectrum analyzer 180. It should be understood that in some embodiments, the modulated electromagnetic signal 140' may be provided directly to the spectrum analyzer 180 without additional amplification by the second amplifier 170.

The spectrum analyzer 180 is configured to sample the spectrum data of the modulated electromagnetic signal over a desired frequency range. The spectrum analyzer 180 may be configured as any device or circuit capable of sampling the spectrum data of the electromagnetic signal. As an example and not a limitation, the spectrum analyzer 180 includes an HP 8560E spectrum analyzer manufactured by Hewlett-Packard. Any spectrum analyzer may be used.

The spectrum analyzer 180 may be communicatively coupled to a computing device 190, which may take on a wide variety of configurations. The computing device 190 may include, but is not limited to, a general-purpose computer, a special-purpose computer, a laptop computer, a tablet computer, a mobile device, or a proprietary microcontroller circuit. In one embodiment, the functionality of the spectrum analyzer 180 is provided by the computing device 190 such that the functionalities of both components are integrated into a signal component.

The computing device 190 is configured to receive the sampled spectrum data of the modulated electromagnetic signal 140' and calculate an evaluation parameter $\Delta$. As described in detail below, the evaluation parameter $\Delta$ is indicative of the neurological status of the biological tissue under evaluation 12. In an alternative embodiment, the evaluation parameter $\Delta$ is calculated by the spectrum analyzer 180 and is provided to the computing device 190. The computing device 190 may use the evaluation parameter $\Delta$ to provide a neurological status indicator to the operator of the neurological status evaluation apparatus. For example, the computing device 190 may compare the evaluation parameter $\Delta$ to one or more sample evaluation parameters $\Delta$ that are indicative of the existence of particular neurological events or conditions within the biological tissue under evaluation 12 (e.g., ICH, intra-cranial pressure (ICP), cerebral edema, seizure activity, and the like). The evaluation parameter $\Delta$ may indicate the existence of a neurological event or condition based on the changes in the dielectric properties of the living tissue under evaluation that are caused by such a neurological event or condition.

The computing device 190 may then output the neurological status indicator to the operator. The neurological status indicator may include, but is not limited to, graphics displayed on a graphical display device associated with the computing device 190 (e.g., a liquid crystal display screen), a text message displayed on the graphical display device associated with the computing device 190, numerical values displayed on the graphical display device, light emitting diodes associated with the computing device 190, auditory messages, and wireless transmission to an external computing device.

As stated above, the embodiments described herein may measure the changes in an electromagnetic signal induced by passage through the cranium of a human head to determine if a significant change in patient neurologic status has occurred. In one embodiment, a neurological status evaluation apparatus is operable to detect acute small hemorrhages (<3 ml) and brain edema such as can occur as a result of traumatic brain injury.

Electromagnetic fields interact with the charges and ions contained in biological tissue. At low frequencies (~MHz), such fields induce ionic motion and currents such that there is energy lost from the electromagnetic wave in doing the work to move these charges. As a result, the electromagnetic absorption and scattering of biological tissue at lower frequencies is very dependent upon the ionic solute quantity of the tissue. This electromagnetic absorption process is known as the beta ($\beta$) dispersion of electromagnetic fields.

At higher frequencies (~GHz), the ionic mobility becomes more limited in biological tissue and fluids. As a result, the $\beta$ dispersion of electromagnetic fields is reduced. Electromagnetic interactions in this frequency regime are dominated by the interaction of the electric dipoles of water molecules with the electromagnetic field. This absorbs energy from the fields as the water molecules absorb energy, a process called gamma ($\gamma$) dispersion. Overall, $\beta$ dispersion dominates for frequencies less than 1 GHz, while $\gamma$ dispersion is more important for frequencies greater than 3 GHz.

Christ et al. recently introduced a model of the interaction of electromagnetic absorption in layered biological tissues (Christ A, Samaras T, Klingenbock A, and Kuster N., "Characterization of the electromagnetic near-field absorption in layered biological tissue in the frequency range from 30 MHz to 6,000 MHz." *Phys Med Biol* 51: 4951-4965, 2006). If an electromagnetic wave of wave vector k is propagating in the z-direction normal to the tissue plane, one can write the electric field components as:

$$E_i(k,z) = E_i^{incident} e^{ikz} + E_i^{reflected} e^{-ikz - i\phi}, \quad \text{Eq. (1)}$$

where the components of E are transverse to k, and consist of incident and reflected components.

The peak average specific absorption rate (SAR), which is the power loss from the electromagnetic field in tissue per unit volume, can then be estimated as:

$$SAR(k, m) \approx \frac{A}{2m} \int_0^l dz \sigma |E_{PEAK}(k, z)|^2, \quad \text{Eq. (2)}$$

where the electromagnetic wave is incident normally on the tissue, the tissue has mass m over area A with thickness l, and conductivity $\sigma$. In addition, $E_{PEAK}$ is the maximum amplitude of E over the tissue thickness l. It should be noted that $\sigma$ depends on the frequency of the electromagnetic wave, as discussed above. Also, changes in the permittivity $\varepsilon$ within the tissue can result in some of the incident electromagnetic energy being reflected from the various interfaces. In addition, it is implicitly assumed in Eq. (2) that the electric field E penetrates the entire tissue volume; thus Eq. (2) neglects "shielding" effects.

This approach can be generalized to tissues with conductivity and permittivity varying in the z-direction. Again, assuming that the electromagnetic wave is incident normally on the tissue, and allowing the conductivity $\sigma$ and permittivity $\varepsilon$ to vary as a function of z, one can write an approximate expression for the magnitude of the electric field E(z) as $$E(z) \approx E_o e^{-\kappa(z) z}, \quad \text{Eq. (3)}$$

where $E_o$ is the incident amplitude of the electric field, and $\kappa$ can be written as:

$$\kappa \equiv \omega \sqrt{\frac{\varepsilon \mu}{2}} \left\{ \sqrt{\left(\frac{\sigma}{\varepsilon \omega}\right)^2 + 1} - 1 \right\}^{1/2}, \quad \text{Eq. (4)}$$

where $\mu$ and $\varepsilon$ are the permeability and permittivity of the tissue respectively, and $\omega$ is the angular frequency of the electromagnetic signal. Note that both $\varepsilon$ and $\mu$ are implied functions of z as well. Generalizing Eq. (2) yields:

$$SAR \approx \frac{A}{2m} |E_o|^2 \int_0^l dz \sigma(z) e^{-2\kappa(z)z}, \quad \text{Eq. (5)}$$

where l is the total tissue width along the z-direct, as above.

It is interesting to take the limit for SAR of small $\sigma$. This yields the expression:

$$SAR \approx \frac{A}{2m} |E_o|^2 \int_0^l dz \sigma(z) e^{-\sigma(z)(\mu/\varepsilon)^{1.2} z}. \quad \text{Eq. (6)}$$

This is the frequency-independent limit for $\kappa$, and is a reasonable approximation in poor conductors. Note that to leading order in $\sigma$, the SAR is linear in $\sigma$ and therefore to small changes in this parameter. Also note that small changes in $\varepsilon(z)$ can substantially change the SAR either increasing or decreasing the magnitude of this parameter.

It would be useful to relate Eq. (6) to a measurable parameter that can be obtained in a real system. In a given antenna, an incident electric field induces a time varying voltage at the antenna terminals, as expressed by:

$$V = \alpha E, \quad \text{Eq. (7a)}$$

where V is the output voltage of the antenna, E is the magnitude of the incident electric field, and $\alpha$ is a constant which depends on the detailed electrical parameters of the antenna.

The measured power at the antenna terminals then approximately becomes:

$$P \approx \int_{\omega 1}^{\omega 2} d\omega \left( \frac{V^2(\omega)}{Z(\omega)} \right), \quad \text{Eq. (7b)}$$

where the integral is taken over the antenna's finite bandwidth ($\omega_1$, $\omega_2$) around the electromagnetic signal frequency $\omega_0$, and $Z(\omega)$ is the magnitude of the antenna impedance. If we assume the antenna configuration of FIG. 1 with no brain present, we can define the measured power difference ($\Delta$) between the two antennas as:

$$\Delta \equiv \int_{\omega 1}^{\omega 2} d\omega \left( \left( \frac{V^2(\omega)}{Z(\omega)} \right)_T - \left( \frac{V^2(\omega)}{Z(\omega)} \right)_R \right) = \int_{\omega 1}^{\omega 2} d\omega \left( \frac{E_T^2}{\alpha_T^2 Z_T(\omega)} - \frac{E_R^2}{\alpha_R^2 Z_R(\omega)} \right), \quad \text{Eq. (8a)}$$

where the explicit dependence on E from Eq. (7a) has been substituted. This is the evaluation parameter $\Delta$ described above. The subscripts T and R denote parameters for the transmitting and receiving antenna, as discussed above. Assuming that the transmitting and the receiving antennae are identical such that the denominators in Eq. (8a) are equivalent, Eq. (8a) may be expressed as:

$$\Delta \equiv K \int_{f_o}^{f_1} df (|E_T(f)|^2 - |E_R(f)|^2).  \quad \text{Eq. (8b)}$$

where $E_T(f)$ is the transmitted signal (from T) as a function of frequency f, $E_R(f)$ is the received signal (from R), K is constant which contains the antennae parameters, and $f_0$ and $f_1$ are the portions of the frequency spectrum over which the summation is performed.

If the brain (or other biological tissue) is placed between the transmitting and receiving antennas 130, 150, the received power will change due to electromagnetic absorption in the brain. An approximate expression for this loss may be derived by generalizing Eq. (5) to three dimensions yielding:

$$SAR_{Brain} \approx G_{Brain} \int_{Brain} d^3 r \sigma(r, \omega) |E(r)|^2 e^{-2\kappa(r,\omega)z}, \quad \text{Eq. (9)}$$

where r is the position vector within the brain, $G_{Brain}$ contains the geometric factors of the sample brain in this model, and the frequency dependence of σ and κ has been made explicit. For convenience, it is assumed that the wavevector k of the electromagnetic signal is oriented along the z axis, and the origin is placed on the surface of the brain. Therefore, the measured $\Delta_{Brain}$ will be approximately related to $\Delta_{NoBrain}$ by:

$$\Delta_{NoBrain} - \Delta_{Brain} \approx SAR_{Brain} \quad \text{Eq. (10)}$$

Note that Eqs. (9) and (10) are only an approximate model, as it is assumed that: (1) the incident electromagnetic signal is a plane wave, and (2) these expressions implicitly assume "far field" electromagnetic behavior. Assumption 2 holds for distances less than $(\lambda/2\pi)$ where λ is the wavelength of the electromagnetic signal. The near field dimension ranges from 2.5 to 12.5 cm for frequencies of 1.2 to 0.4 GHz respectively. Being in the near field regime results in the evaluation parameter being more sensitive to geometric changes in brain structure and may actually increase overall changes in the evaluation parameter Δ for small tissue shifts in the brain.

Figure 2:
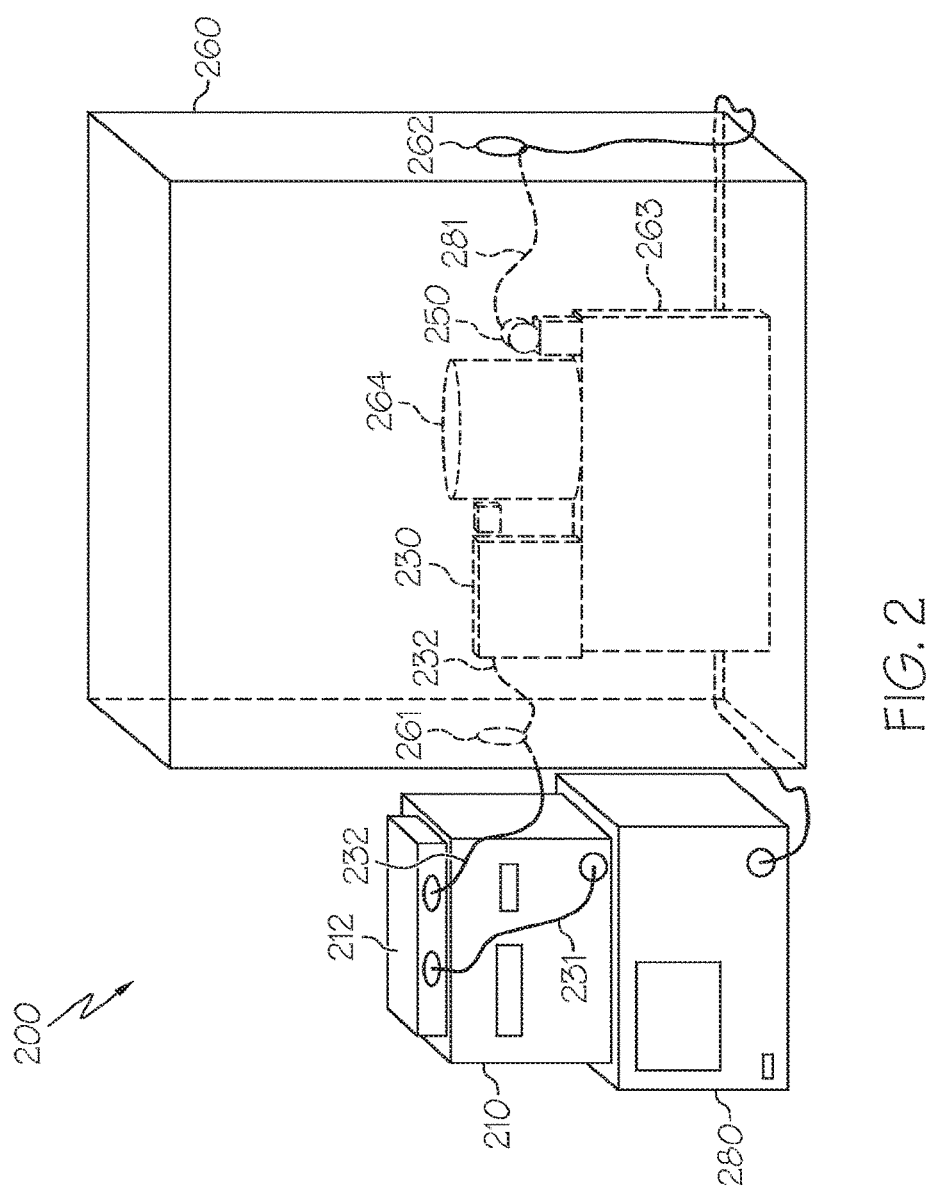
FIG. 2 depicts a schematic illustration of a neurological evaluation apparatus according to one or more embodiments shown and described herein.

Referring now to FIG. 2, a prototype neurological status evaluation apparatus 200 was constructed in accordance with the schematic of FIG. 1. It should be understood that embodiments are not limited to the components and configurations depicted in FIG. 2. A Hewlett-Packard signal generator 210 (HP 8557B) was used to generated the electromagnetic signal. The signal generator 210 was electrically coupled to a radiofrequency amplifier 212 (ENI607L, manufactured by ENI of Rochester, N.Y.) by electrical conductors 231. The transmitting antenna 230 was configured as a PCB Log Periodic WA5VJB antenna manufactured by Ramsey Electronics of Victor, N.Y., and the receiving antenna 250 was configured as a SATCOM UL-3001-340-CF portable UHF antenna manufactured by Myers Engineering International, Inc. of Marget, Fla. The transmitting antenna 230 and the receiving antenna 250 were positioned on a platform 263 within a 30"×33"×40" Faraday cage 260 manufactured by Automate Scientific, Inc. of Berkeley, Calif. The output of the radiofrequency amplifier 212 was coupled to the transmitting antenna 230 via an electrical conductor 232 that passed through a hole 261 in the Faraday cage 260. The receiving antenna 250 was coupled to a spectrum analyzer (HP 8560E by Hewlett-Packard of Palo Alto, Calif. via an electrical conductor 281 that passed through a hole 262 in the Faraday cage 260.

The prototype neurological status evaluation apparatus 200 was constructed to detect an in vitro intracranial hemorrhage (ICH) or a subarachnoid hemorrhage (SAH), an in vivo porcine model of ICH, and an ex vivo porcine model of SAH. These two examples are described in detail below.

In Vitro Experiments—Example 1

A "brain mimicking" gelatin was made to simulate the low-frequency conducting properties of human brain tissue in the shape of a cylinder with a total weight of approximately 1 kg. First, 0.75 grams of pure NaCl were added to one liter of filtered deionized water. Then 56 grams of commercial gelatin were mixed into the one liter 0.75 g/L saline solution using a hot plate with magnetic stirrer to ensure consistent concentration throughout the gel. After all the gelatin had dissolved, the gel was then cooled and placed in a 4° C. refrigerator to solidify overnight.

The transmitting and receiving antennas 230, 250 were placed on the platform 263 at the same level 15 cm apart so that their highest point was ⅔ of the height of the gelatin model 264, about 7 cm high. The platform 263 was 22 cm above the bottom of the Faraday cage 260. When the gelatin model 264 was present during an experiment, it was always placed in the same location between the transmitting and receiving antennas 230, 250.

The evaluation parameter Δ was measured for the gelatin model absent from the evaluation space between the transmitting and receiving antennas (gel −) and the gelatin model 264 present in the evaluation space between the transmitting and receiving antennas (2) gel (gel +). The signal generator 210 produced a 1 MHz signal at a constant amplitude of 1.5V that was then provided to the radiofrequency amplifier 212, which in this experiment amplified the electromagnetic signal by 7.0 dB. All input impedances were 50Ω. The frequency spectra were integrated over from 0.8 MHz ($f_0$) to 1.2 MHz ($f_1$); it has been shown that changing these limits does not alter the measured evaluation parameter to any significant degree.

An ICH model was created after the evaluation parameter Δ values for the gel (−) and gel (+) groups were obtained. A gelatin model was cut in half, and a small hole created within the gel. This hole was then filled with 50 cc of citrated human blood to simulate an ICH, and the evaluation parameter Δ for this ICH model configuration was measured, as described above.

Figure 3:
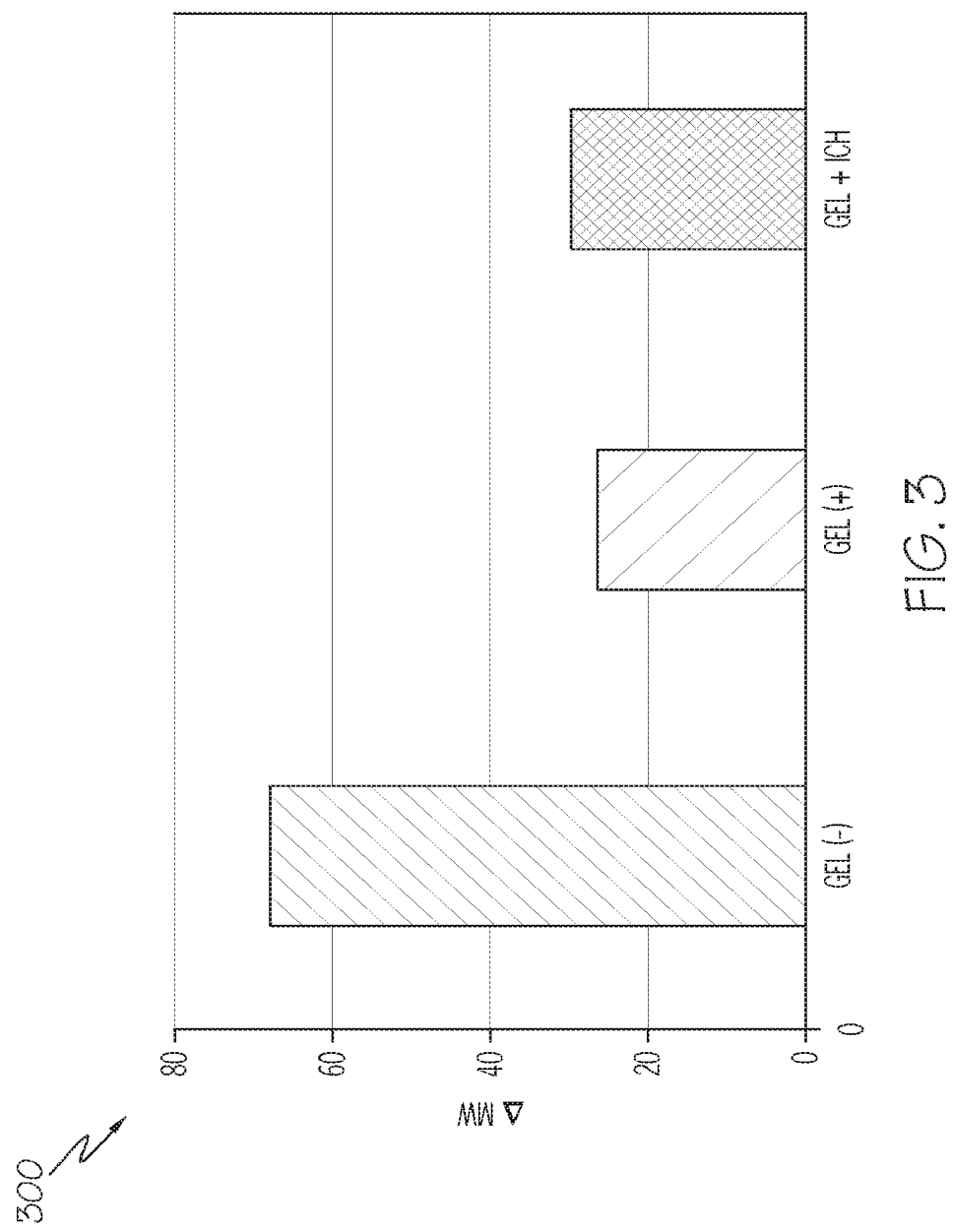
FIG. 3 depicts a graph plotting an evaluation parameter Δ as a function of a treatment group of an exemplary experiment according to one or more embodiments shown and described herein.

The proof of principle trials for each configuration were performed, and two gels were used in these experiments for an n=6 for each study group. A t-test was used to determine if the experimental groups were different (p≤0.05). FIG. 3 illustrates a graph 300 that shows the evaluation parameter Δ as a function of treatment group. The values for the gel (+) and gel+ICH groups are significantly different (p<0.05), differing by about 12% overall. Accordingly, the 1 MHz prototype device is capable of detecting 50 CC of blood in an in-vitro human brain model.

In Vitro Experiments—Example 2

In this example, the ICH model consisted of a blood-filled cylindrical cavity in the center of the brain-mimicking gelatin, about 6 cm from the bottom. Wire was used to cut through the gelatin, making a cap at about 8 cm from the bottom. Next, a plastic cylinder of the volume being tested (0.5, 1, 3, 5, 10, or 20 ml) was inserted into the center of the gelatin and removed, thereby removing that volume of gelatin. The blood used was human Quantity-Not-Sufficient blood (not enough blood is present to be used for donation) purchased from a local blood center. The cavity was filled with blood and the cap replaced to create the ICH model.

Spectrum data was collected every 3 seconds using MATLAB (Mathworks Inc., Natick, Mass.; v.7.10.0.499). The received power was collected over a bandwidth of 10 MHz with the center frequency at 400 MHz. The 601 numerical values which represented the curve on the spectrum analyzer display were input into MATLAB and integrated numerically to determine the total output power received at the receiving antenna 250 ($P_R$). The evaluation parameter $\Delta$ is then defined as:

$$\Delta = P_R(\text{ICH}) - P_R(\text{gel}), \qquad \text{Eq. (11)}$$

where the experimental groups are defined below.

Ten measurements were made for three different experiments in each gelatin sample: the empty cage (control), when the gel was present (gel), and when the gel and blood filled cavity (ICH model) were present. Evaluation parameters for the average and standard deviation were then computed for each experimental group. Student's paired t-test was used to determine if values of evaluation parameter $\Delta$ were significantly different from zero. A $p<0.05$ was considered to be significant.

Figure 4:
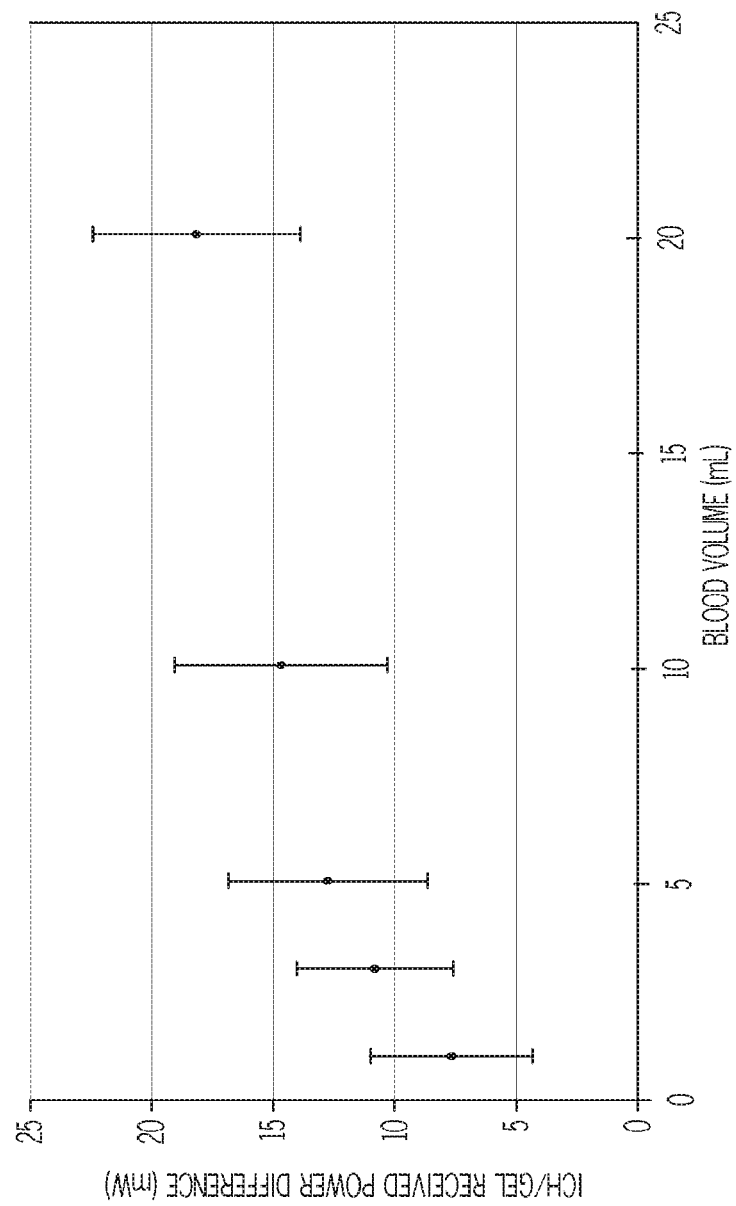
FIG. 4 depicts a graph plotting an average evaluation parameter Δ for a plurality of intracranial hemorrhage volumes of an exemplary experiment according to one or more embodiments shown and described herein.

The evaluation parameter $\Delta$ was measured for ICH volumes 1, 3, 5, 10, and 20 ml. The average received power for the gel-only measurement across ten trials was 522 mW with a standard deviation of 21 mW. The average for the ICH model across ten trials was 535 mW with a standard deviation of 19 mW. The difference between the gel-only and the ICH model was statistically significant ($P<0.001$) for all blood volumes greater than or equal to 1.0 ml. The data are shown in FIG. 4.

Overall, the difference among the treatment groups are significant ($p<0.05$). The minimum resolvable blood volume that can be approximately resolved in this configuration is ~1.0 ml (95% confidence level). It is also noted that the evaluation parameter $\Delta$ scales with the cross-sectional surface area of the blood collections used in these experiments. Given that the cylindrical blood collection has a known radius $\rho$, and a height h, the cross-sectional area is defined as:

$$A = 2\rho h, \qquad \text{Eq. (12)}$$

Figure 5:
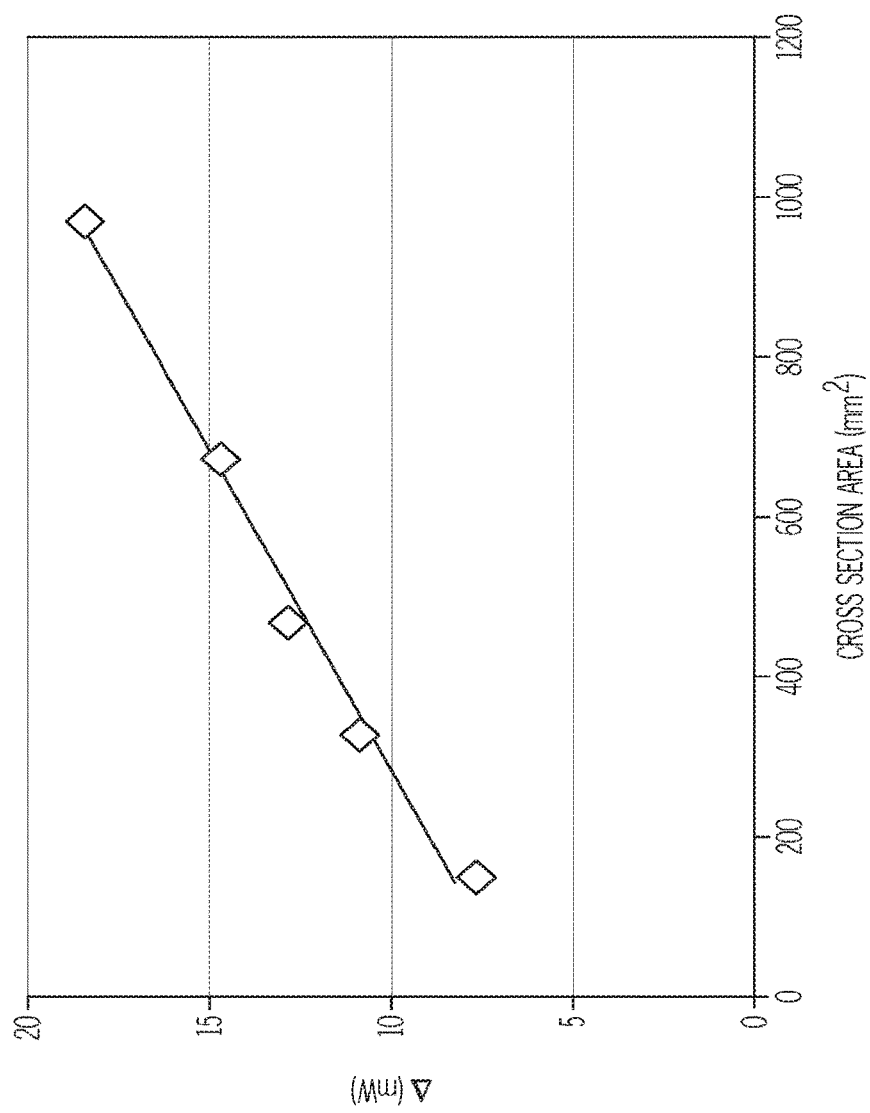
FIG. 5 depicts a graph illustrating the values of the evaluation parameter Δ for each intracranial hemorrhage volume as a function of area for an exemplary experiment according to one or more embodiments shown and described herein.

FIG. 5 illustrates the values of the evaluation parameter $\Delta$ for each volume as a function of A. The error bars are not shown for clarity.

The in vitro experiments demonstrate the ability of the prototype neurological status evaluation apparatus to detect volumes of blood as small as 1 ml. In addition, the parameter evaluation parameter $\Delta$ scales with the cross-sectional area of the blood volume. This latter finding is physically sensible as the proportion of the electromagnetic signal that can interact with the blood volume is proportional to the cross sectional area.

In Vivo ICH Experiments—Example 3

In these experiments, the goal was to verify the ability of the neurological status evaluation apparatus 200 depicted in FIGS. 1 and 2 to detect ICH in an in vivo porcine model of ICH. These experiments utilized the well-established approach of Wagner et al. in their experimental ICH model. In a given experiment, a juvenile pig was sedated and intubated using ketamine, after IACUC approval. Anesthesia was continuously maintained using pentobarbital, and the pig's hemodynamic status was monitored throughout the experiment. After intubation and sedation, the neurological status evaluation apparatus 200 was positioned such that the maximal signal intensity from the transmitting antenna 230 was incident normally to the lateral canthus of the porcine eye. The receiving antenna 250 was aligned to maximize the received power from the transmitting antenna 230. A total n=2 pigs were used in the current study; an additional five pigs were used for validation.

A silastic catheter was placed through the frontal bone into the frontal lobe. After catheter placement, the evaluation parameter $\Delta$ (denoted $\Delta(-\text{ICH})$) was measured using the previously described setup for Example 2, excluding the Faraday cage 260, which was not used in these experiments. After this measurement, 3 ml of autologous porcine blood was infused into the porcine frontal lobe, and the evaluation parameter $\Delta$ was measured again ($\Delta(+\text{ICH})$).

Figure 6A:
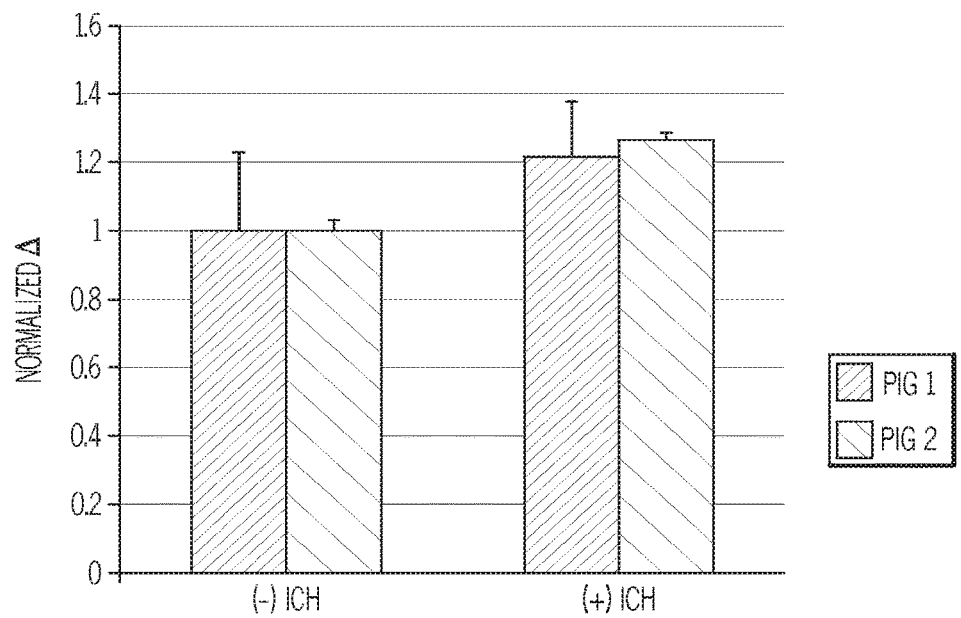
FIG. 6A depicts a graph illustrating the evaluation parameter Δ for each treatment group in an exemplary in vivo porcine model experiment according to one or more embodiments shown and described herein.

FIG. 6A graphically illustrates the evaluation parameter $\Delta$ for each treatment group, and the error bars are the standard deviations of the data. The data are normalized to the average $\Delta(-\text{ICH})$ value for each pig to compare experiments. On average, the presence of the 3 ml ICH increases the evaluation parameter $\Delta$ by 22% for pig 1, and 26% for pig 2. For both experiments (and subsequent confirmatory five experiments), the $-$ICH and $+$ICH groups are significantly different ($p<0.05$).

These in vivo experiments verify the more detailed in vitro results discussed above. It has been demonstrated that the prototype neurological status evaluation apparatus 200 operating at 400 MHz is capable of detecting as little as 3 ml of acute hemorrhage in an in vivo porcine ICH model.

Ex Vivo SAH Experiments—Example 4

After appropriate IACUC approval of the protocol, a cadaveric porcine head was obtained after animal sacrifice. A midline incision was then made in the scalp of the animal. The scalp was then bluntly dissected away from the periosteum of the skull, and a 4 cm circular bone flap created, without harming the underlying dura or brain. The dura was carefully incised in the midline using a #11 scalpel, and bluntly dissected away from the brain using a Kelly clamp exposing the brain.

In order to simulate subarachnoid hemorrhaging (SAH), approximately 3 ml of citrated human venous blood was injected between the dura and the brain. The experimental setup and procedure is otherwise as above. An n=5 measurement were made using the prototype neurological status evaluation apparatus 200 for each treatment group. The prototype neurological evaluation apparatus 200 was operated at the parameters described above with respect to Examples 2 and 3. The treatment groups were: control (no head); head without blood, SAH ($-$); and head with blood, SAH ($+$). Student's t-test (paired) was used for comparisons of the treatment groups, and a $p<0.05$ was considered significant. Data are presented as means with standard deviations.

Figure 6B:
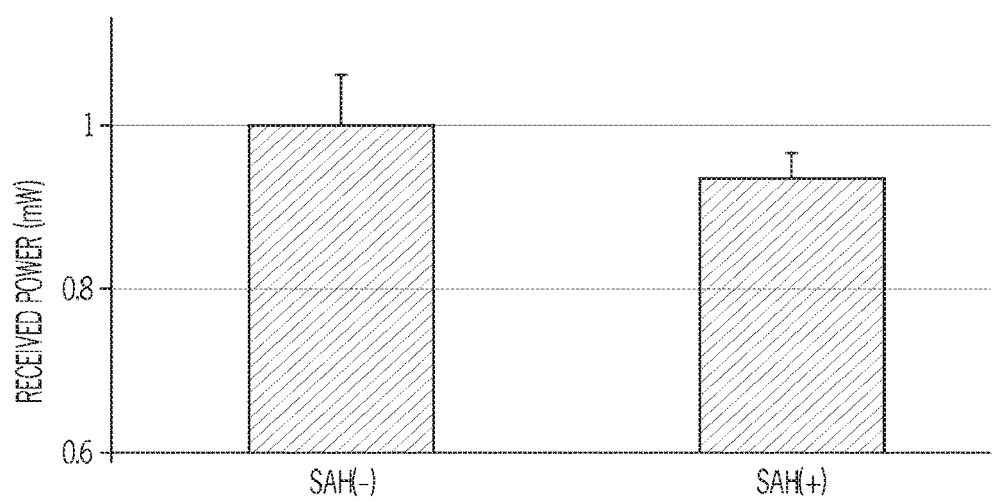
FIG. 6B depicts a graph illustrating the evaluation parameter Δ for each treatment group in an exemplary ex vivo porcine model experiment according to one or more embodiments shown and described herein.

FIG. 6B graphically illustrates the received power of the receiving antenna 250 as a function of treatment group (note that the control group is not shown in FIG. 6B). The SAH ($+$) (0.94$\pm$0.04 mW) was significantly different ($p=0.03$) from the SAH ($-$) group (1.00$\pm$0.06 mW).

It is interesting to note that the received power increases with the experimental hemorrhage in the in vitro experiments and decreases for the ex vivo SAH measurement. This is likely due to the differing conductivities in the two experiments. In the ex vivo experiment, the conductivity of the surrounding bony skull and tissue is likely less than that of blood. As a result, introducing the better conducting blood results in a relative increase in the SAR (Eq. 2) and decreases the received power. However, if the conductivity of the blood is much higher that the material it surrounds, "shielding" of the interior of the blood volume may occur, and reduce the volume which the electric field penetrates.

Figure 7B:
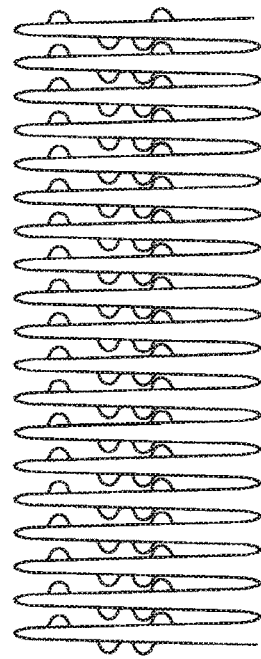
FIG. 7B schematically depicts an exemplary modulated electromagnetic signal according to one or more embodiments shown and described herein.
Figure 7A:
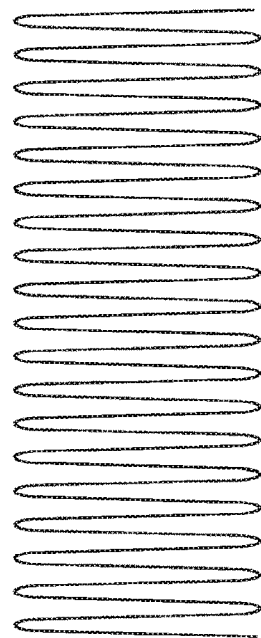
FIG. 7A schematically depicts an exemplary electromagnetic signal according to one or more embodiments shown and described herein.

Referring now to FIG. 7A, an exemplary wave form of an electromagnetic signal transmitted by the transmitting antenna 130 is schematically shown. As described above, the exemplary electromagnetic signal crosses the patient's brain and is received as a modulated electromagnetic signal at the receiving antenna 150. An exemplary wave form of a modulated electromagnetic signal is schematically shown in FIG. 7B. It is noted that FIG. 7B is only a schematic representation of the modulated electromagnetic signal and does not illustrate changes such as amplitude modulation, for example. The waveform has changed due to noise and absorbance characteristics of the brain, and neurological events, such as blood, blood clot, edema, seizure activity, and the like.

Figure 7C:
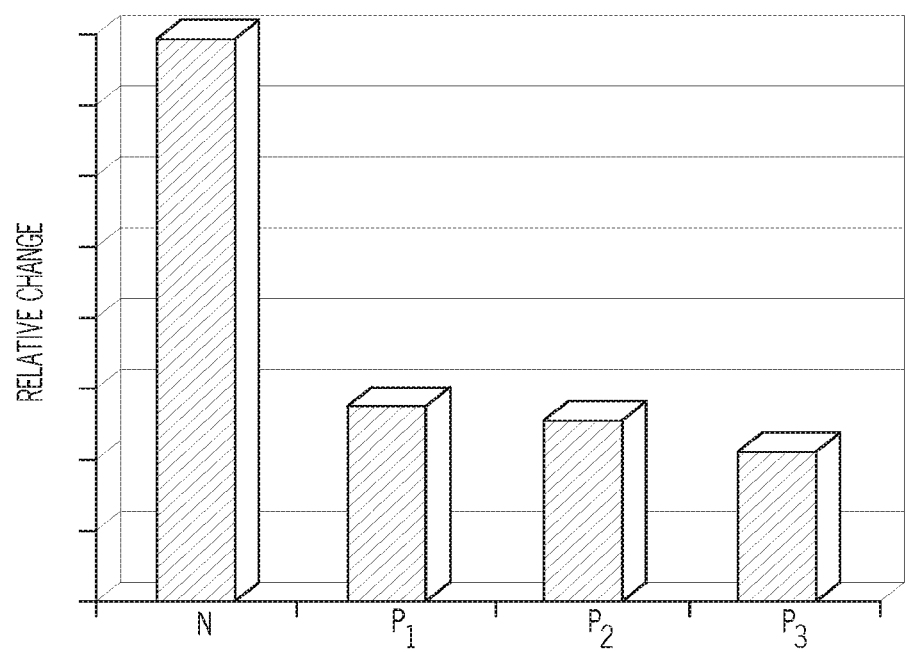
FIG. 7C depicts a graph illustrating a exemplary relative evaluation parameter responses of the modulated electromagnetic signal for various pathologies according to one or more embodiments shown and described herein.

In some embodiments, the modulated electromagnetic signal is transformed (e.g., by a Fourier transformation), to extract spectrum data. Multiple frequency sweeps may be transformed to produce a transformation of the modulated electromagnetic signal. FIG. 7C graphically illustrates exemplary relative change in the evaluation parameter for total normal brain (N), and several pathologies ($P_1$-$P_2$). As shown in FIG. 7C, different neurological events or conditions (e.g., bleeding, blood clot, and cerebral edema) produce different evaluation parameter responses such that particular neurological events or conditions may be differentiated.

Figure 8:
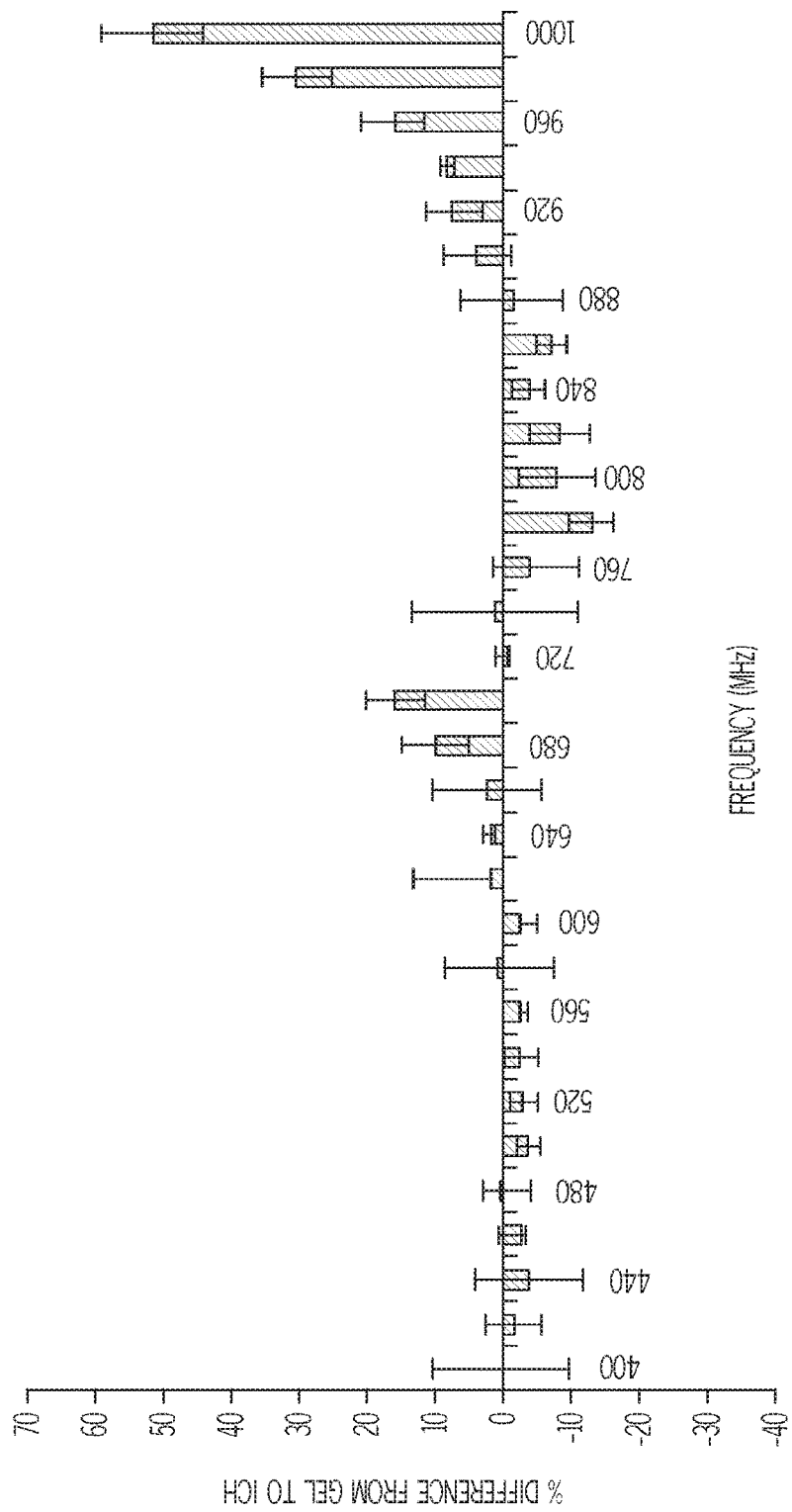
FIG. 8 graphically depicts a difference in the evaluation parameter Δ between a brain-mimicking gelatin model and an ICH model by frequency according to one or more embodiments shown and described herein.

The frequency chosen for the electromagnetic signal may depend on the neurological event that is being detected. For example, the frequency of an electromagnetic signal used to detect ICH may be different from the frequency used to detect a seizure. FIG. 8 is a graph that plots the difference in the evaluation parameter Δ of the gelatin only with respect to the evaluation parameter Δ of the ICH model against frequency according to a simulation. According to the graph of FIG. 8, 1 GHz has the best signal-to-noise ratio. In one embodiment, the neurological status evaluation apparatus may be configured to operate at a frequency between about 1 MHz and about 2 GHz. It should be understood that other pathologies may produce other frequency response characteristics within various frequency ranges, which may be useful for detecting other pathologies using the same or other frequencies or frequency ranges.

Figure 9A:
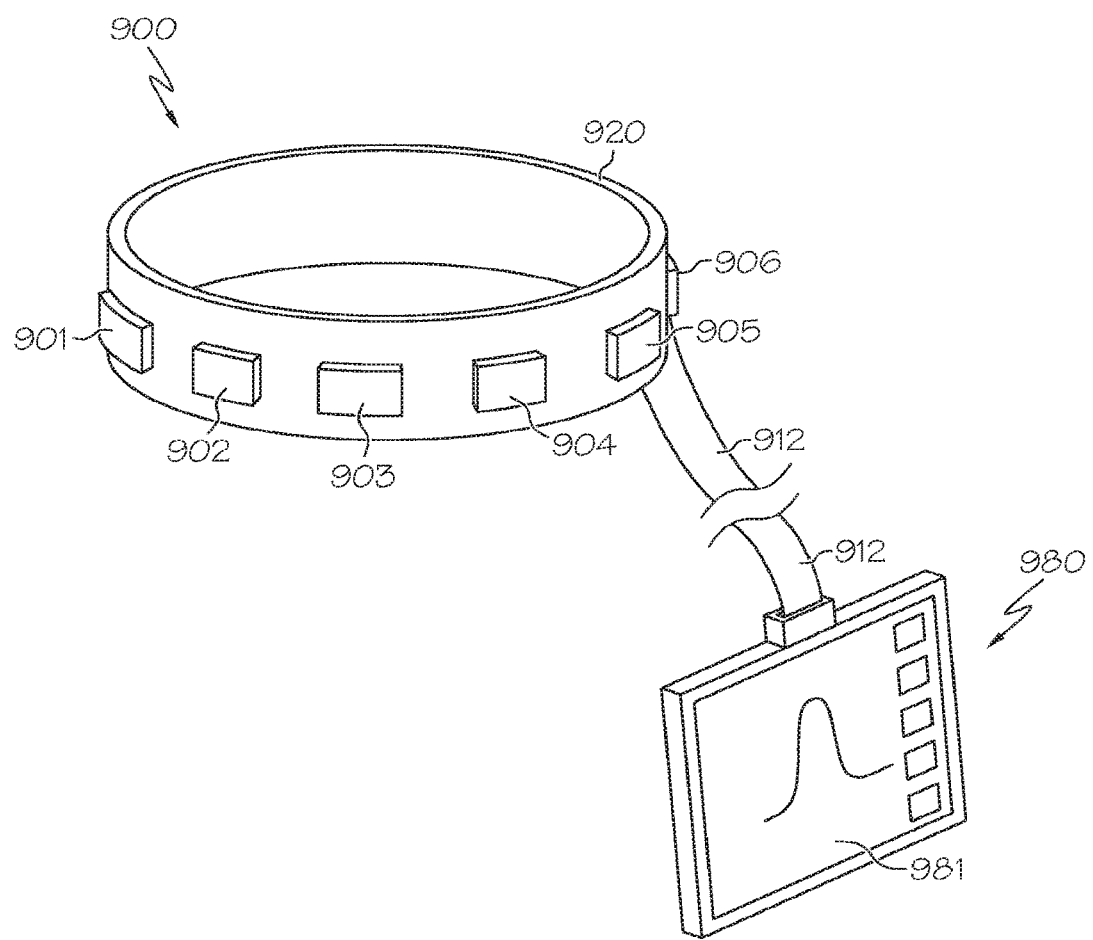
FIG. 9A schematically depicts an exemplary transcranial neurological evaluation apparatus according to one or more embodiments shown and described herein.

Referring now to FIG. 9A, a portable transcranial neurological evaluation apparatus 900 is illustrated. The transcranial neurological evaluation apparatus 900 generally comprises a plurality of transceiver devices 901-912 positioned around a circumference of a headband portion 920 that is configured to be positioned onto the head of a portion without the transceiver devices 901-912 physically contacting the patient's head. The transcranial neurological evaluation apparatus 900 is a non-invasive, trans-cranial, trans-dermal sensor that is operable to detect blood deep in the brain and near the surface and provide volume and location information concerning that blood in TBI (and stroke) patients.

The headband portion 920 may be configured as a fabric, gauze, or other flexible material that is not electrically conductive. Each transceiver device 901-912 comprises a transmitting antenna and a receiving antenna such that it may both transmit and receive electromagnetic signals. The transmitting antenna may transmit the electromagnetic signal, and the receiving antenna may receive the modulated electromagnetic signal after propagating through the patient's cranium, as described above. Each transceiver device is paired with another transceiver device located at an opposite section of the headband portion 920.

Figure 9B:
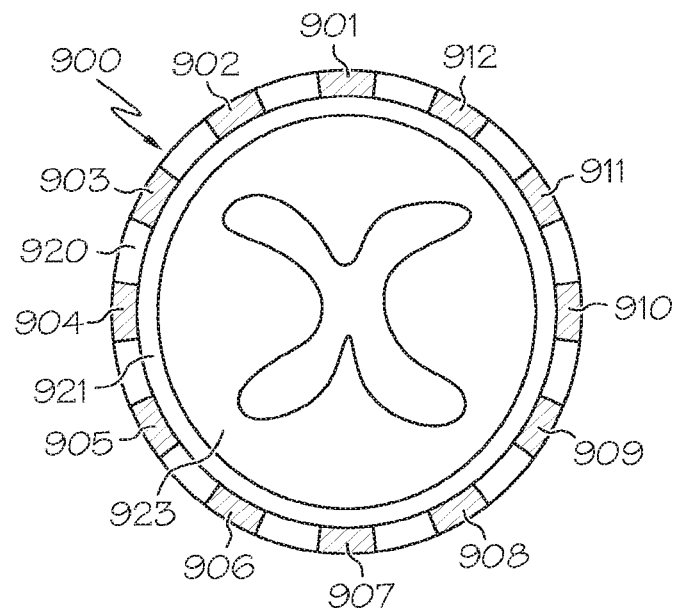
FIG. 9B schematically depicts an exemplary transcranial neurological evaluation apparatus positioned on a human head according to one or more embodiments shown and described herein.

Any number of transceiver devices may be utilized. In order to achieve 95% coverage of the brain's volume for detecting bleeding, multiple pairs of transmitting and receiving antennas may be used. In one embodiment, eight pairs of transceiver devices are used. In another embodiment, the transcranial neurological evaluation apparatus 900 comprises a first row of transceiver devices in a first horizontal plane, and a second row of transceiver devices in a second horizontal plane (e.g., one row of eight transceiver devices on top of another row of transceiver devices around the circumference of the headband portion 920). Twelve transceiver devices are depicted in FIGS. 9A and 9B for ease of illustration.

A combination of a de-multiplexer (de-mux) and multiplexer (mux) can be used to accomplish the creation of an array (in pairs) of the antennas of the transceiver devices. A de-mux may connect a single transceiver to any of the user selected transmitting antennas. The receiving antennas may be connected to a mux which may have a single output to a spectrum analyzer. In one embodiment, the spectrum analyzer (not shown in FIG. 9A) is a separate, handheld component (e.g., a handheld computing device 980) operated by the user of the transcranial neurological evaluation apparatus 900. In another embodiment, the spectrum analyzer is incorporated into the headband portion 920).

In some embodiments, a smart sensor system may be provided that can detect head thickness as well as correct for poor placement, skull shape or movement of the headband while covering 95% of the brain's volume. A smart sensor algorithm may detect the transceivers that are aligned and working properly and thereby focus on those transceivers for diagnostic and monitoring. Thus, if transcranial neurological evaluation apparatus 900 is deployed with an array of four pairs of transmitters and receiving antennas, the smart sensor system can use all four if capable, or only the pairs that respond according to set thresholds. Accordingly, the smart sensor system can correct for poor placement, skull shape or movement of the headband.

A microprocessor (e.g., a microprocessor included in the handheld computing device 980) may digitally select the correct corresponding pair of antennas, collect necessary data from the spectrum analyzer, and repeat the process until data from all pairs have been collected. In the embodiment depicted in FIG. 9A, the transceiver devices 901-912 are electrically coupled to a computing device 980 by a wired connection 912. Signal amplitude for each antenna pair and configuration data (e.g., a size of the patient's head) may be stored.

In some embodiments, data from the transceiver devices 901-912 may be provided to the computing device 980 wirelessly. Power to the transceiver devices 901-912 may be provided by the wired connection 912, or by a power supply located on the headband portion 920.

The computing device 980 may take on a variety of configurations, such as a general purpose computer, a specific purpose computer, a laptop computer, a tablet computer, a smart phone, and the like. As stated above, the functionality of the spectrum analyzer and the computing device 980 may be performed entirely by the computing device 980. The computing device 980 may be capable of conveying neurological status indicator on a graphical user interface 981. Data, including, but not limited to, the neurological status indicator, may also be transmitted to one or more remote computing devices.

Referring now to FIG. 9B, a top view of a transcranial neurological evaluation apparatus 900 applied to a human head comprising a skin and skull layer 921 and a brain 923 is illustrated. Each transceiver device 901-912 has a paired transceiver device associated therewith. For example, transceiver device 904 is paired with transceiver device 910. In one embodiment, the transmitting antenna of each transceiver device 901-912 of the plurality of transceiver devices is activated sequentially to transmit the electromagnetic signal through the skin and skull layer 921 and brain to be received by the receiving antenna of the remaining transceiver devices. As an example and not a limitation, the transmitting antenna of transceiver device 904 may transmit an electromagnetic signal as described above, which is then received by the receiving antenna of transceiver devices 907-912.

When the electromagnetic radiation of the electromagnetic signal is incident on the biological tissue, part of it will be reflected back, and part of it will be transmitted and/or scattered into or away from the medium. For electromagnetic radiation passing through an ICH deep inside the brain, the electric field intensities will interact with multiple media at multiple boundaries. A simplified model is shown below:

Air|Skin|Bone|Brain Tissue|Blood/Hemorrhage|Brain tissue|Bone|Skin|Air

The transcranial neurological evaluation apparatus 900 should account for the air-skin interface without the use of gels or conduction media because it is to be field deployable. The transcranial neurological evaluation apparatus 900 may account for this interface in part by detecting the total volume and circumference of the head. At each of these interfaces, the radiation is deflected by an angle $\alpha_2$, which then becomes the incident angle for the next layer. The incident wave would have undergone reflection and transmission at each of the boundaries and absorption in each of the media, the extent of which is determined by the dielectric properties of each of the media.

The fate of the radiation would be different when passing through a subdural hematoma, modeled as a thin film of blood between the brain tissue and skull:

Air|Skin|Bone|Blood/Hemorrhage|Brain tissue|Bone|Skin|Air

The array of transceiver device 901-912 can be used to measure the properties of an electromagnetic signal transmitted across the brain 923. The resultant signal output may be the result of wave energy absorption, reflection and scattering resulting from the changing dielectric properties of the different media. Different volumes of hemorrhage may impact the incident radiation to different extents depending on the detailed geometry of these volumes. The transceiver devices 901-912 will receive the modulated electromagnetic signal from a given transceiver device after traversing the brain. The highest signal intensity will typically be in the direction of the corresponding transceiver device 901-912. In a TBI patient, the path and medium of the radiation will change due to the injury, presence of new interfaces (blood, brain, CSF etc), and alterations in the electromagnetic properties of that tissue. As a result, in an array of transceiver devices 901-912 surrounding the surface of a head, the receiving antenna of the transceiver device that picks up the highest intensity with respect to the transmitting antenna will also change. This phenomenon can be used to differentiate between different positions of a hemorrhage (subdural hematoma and a deep brain hemorrhage).

Figure 10:
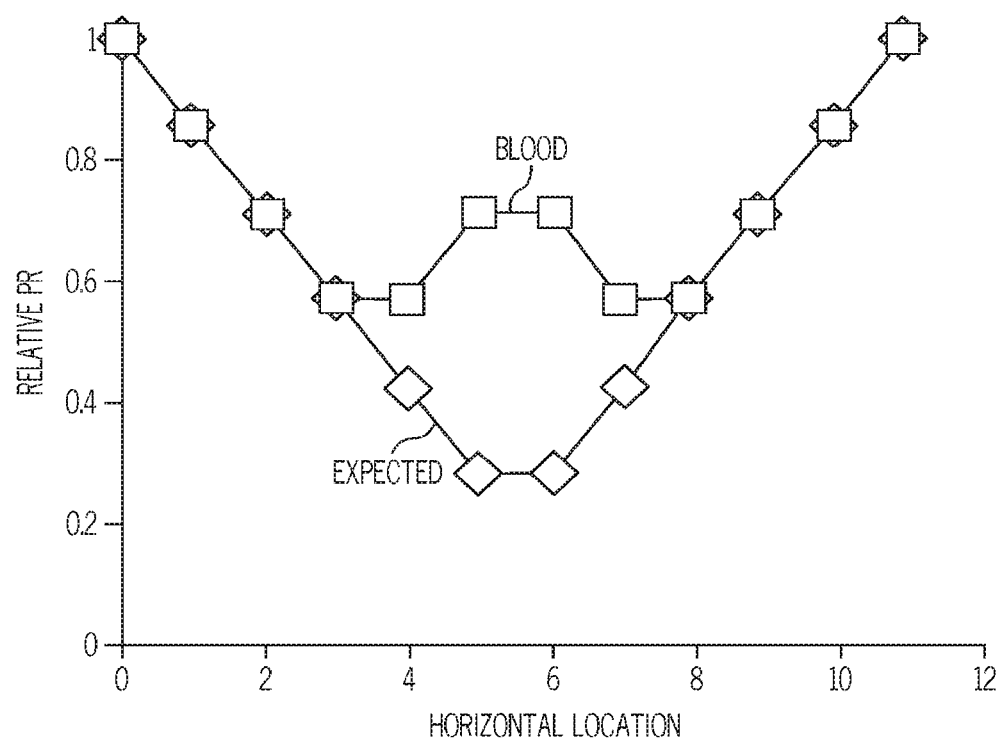
FIG. 10 depicts an exemplary graph plotting relative power of modulated electromagnetic signals received by transceiver devices of a transcranial neurological evaluation apparatus for an expected, normal case and an ICH case according to one or more embodiments shown and described herein.

The present inventors have recognized that blood/hemorrhage within the brain produces an increase in output power of an electromagnetic signal propagating through the blood/hemorrhage region compared to an electromagnetic signal that does not propagate through a blood/hemorrhage region. FIG. 10 graphically depicts a relative power of modulated electromagnetic signals received by a plurality of transceiver devices in an expected, normal case ("Expected"), and in a case of ICH ("Blood"). It is noted that other neurological events or conditions may produce similar grasps as that shown in FIG. 10. Each transceiver device is indicative of a horizontal location about the transcranial neurological evaluation apparatus 900. As an example and not a limitation, referring once again to FIG. 9B, if transceiver device 904 is transmitting the electromagnetic signal, the relative power of the modulated electromagnetic signals received by transceiver devices 901 and 907 will be different than the relative power of the modulated electromagnetic signal received by transceiver device 910 based on the modulation by the tissue between the transmitting device and the receiving devices because of different paths of electromagnetic signal transmission and/or differing electrical properties of the intervening tissue. Data or information from a graph similar to FIG. 10 could contribute to the output information exemplified in FIG. 7C such that the difference between expected and observed pathologies could be graphically presented for various pathologies.

However, as stated above, a transceiver device that receives a modulated electromagnetic signal that passes through a neurological event or condition (e.g., ICH, SAH, and the like) will register a higher relative power than if the neurological event or condition were not present. The curve labeled "Blood" is indicative of blood 940 located at a horizontal location in line with a modulated electromagnetic signal that is received by a transceiver device that is paired with the transmitting transceiver device. In the example wherein transceiver device 904 is the transmitting antenna, the blood 940 is most likely positioned along a direct path between transceiver device 904 and transceiver device 910 because of the increase of power received at the transceiver devices associated with horizontal locations four and five compared to the Expected curve of the graph in FIG. 10. Multiple transceiver devices may transmit the electromagnetic signal to determine a location of the blood 940 within the brain 923.

In this manner, embodiments may be operable to alert field and/or medical personnel if a patient has underlying brain pathology consistent with hemorrhage or edema. It could be deployed on one patient for diagnostics or onto many patients at a mass casualty incident as a set-it-and-forget-it monitor. Lightweight and taking seconds to deploy, the headband array and wireless or wired handheld device can be used as a triage tag with color coding, alarm and text messaging to notify medical personnel of the patient's status. Embodiments may provide an easy to read screen with quantitative and qualitative diagnostic information concerning the presence of hemorrhage in the brain. Embodiments may also be configured to have an automatic call or response option to rapidly establish communication with hospital, helicopter or ambulance teams.

Embodiments described herein may also be utilized to monitor patients for seizure activity. Critically ill patients often require sedation, pharmacological paralysis, and mechanical ventilation, making assessment of neurological status difficult or impossible. Detection of seizures in settings, such as the ICU or NICU, is often impossible without continuous EEG monitoring, which is extremely labor intensive and requires specialization available in only a minority of hospitals. Likewise, paramedical personnel transporting patients to hospitals and emergency room physicians caring for poorly responsive patients are often faced with the question of whether subclinical or non-convulsive seizures are responsible for the patient's presentation. Adequate resources (EEG machines, EEG technicians to apply leads and produce readings, neurologists to read EEGs emergently) are seldom available in these settings to make this diagnosis. There is a particular need for a point-of-care device that detects seizures. There is a particular unmet need for a point-of-care device which can be utilized by medical professionals who are not specialty trained in neurology.

The brain is electrochemically active and there is evidence to suggest that a tailored radiofrequency pulse may interact with the brain in a manner that allows seizure detection. The electrochemical signals produced by the brain during a seizure may change the dielectric properties of the brain. Accordingly, the embodiments described herein may be operable to detect such dielectric property changes resulting from seizures in the manner described above with respect to ICH and SAH. The present inventors hypothesize that the electrochemical activity of the brain may also affect the observed properties of an RF pulse, and that pathological brain activity, such as a seizure, may be distinguishable from normal brain activity by measuring changes in the RF pulse. Embodiments of the neurological status evaluation apparatuses described above (e.g., the apparatuses schematically illustrated in FIGS. 2 and 9A) may be utilized to detect changes in the dielectric properties of a patient's brain to detect a seizure that may be occurring. If a seizure is detected by comparing a current, active evaluation parameter $\Delta$ with a baseline evaluation parameter A, an alarm may be provided to care giver personnel.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A biological status evaluation system, comprising:
a signal generator configured to generate an electromagnetic signal at one or more frequencies;
a transmitting antenna including a transmitting antenna impedance and configured to transmit the electromagnetic signal;
a receiving antenna including a receiving antenna impedance and positioned relative to the transmitting antenna such that an evaluation space is defined between the transmitting antenna and the receiving antenna, wherein the evaluation space is configured to receive a biological tissue; and
a computing device configured to:
analyze a modulated electromagnetic signal after the transmitted electromagnetic signal propagates through the biological tissue,
calculate an evaluation parameter based on an energy difference between the transmitted electromagnetic signal and the modulated electromagnetic signal, wherein the evaluation parameter is indicative of electromagnetic absorption in the biological tissue, and is calculated by:

$$\Delta \equiv \int_{\omega_0}^{\omega_1} \left( \left( \frac{V_T^2(\omega)}{Z_T(\omega)} \right) - \left( \frac{V_R^2(\omega)}{Z_R(\omega)} \right) \right)$$

where:
$\Delta$ is the evaluation parameter,
$V_T$ is the voltage at the transmitting antenna,
$V_R$ is the voltage at the receiving antenna,
$Z_T(\omega)$ is the magnitude of the transmitting antenna impedance,
$Z_R(\omega)$ is the magnitude of the receiving antenna impedance,
$\omega_0$ is a lower bound of a sampled frequency spectrum, and
$\omega_1$ is an upper bound of the sampled frequency spectrum, and
generate a biological status indicator of the biological tissue based on the evaluation parameter.

2. The biological status evaluation system of claim 1, wherein the computing device is further configured to:
determine the energy difference between the transmitted electromagnetic signal and the modulated electromagnetic signal based on electrical properties of the biological tissue; and
calculate the evaluation parameter based on the electrical properties of the biological tissue, wherein the modulated electromagnetic signal as compared to the transmitted electromagnetic signal is altered based on the electrical properties of the biological tissue.

3. The biological status evaluation system of claim 2, wherein the computing device is further configured to:
determine the energy difference between the transmitted electromagnetic signal and the modulated electromagnetic signal based on a dielectric constant of the biological tissue; and
calculate the evaluation parameter based on the dielectric constant of the biological tissue, wherein the modulated electromagnetic signal as compared to the transmitted electromagnetic signal is altered based on the dielectric constant of the biological tissue.

4. The biological status evaluation system of claim 2, wherein the computing device is further configured to:
determine the energy difference between the transmitted electromagnetic signal and the modulated electromagnetic signal based on a conductivity of the biological tissue; and
calculate the evaluation parameter based on the conductivity of the biological tissue, wherein the modulated electromagnetic signal as compared to the transmitted electromagnetic signal is altered based on the conductivity of the biological tissue.

5. The biological status evaluation system of claim 1, wherein the transmitting antenna and the receiving antenna are identical such that:

$$\alpha_T^2 Z_T(\omega) = \alpha_R^2 Z_R(\omega)$$

and the evaluation parameter is calculated by:

$$\Delta = \int_{f_0}^{f_1} df (|E_T(f)|^2 - |E_R(f)|^2),$$

where:
$\alpha_T$ is a constant that depends on a parameter of the transmitting antenna,
$\alpha_R$ is a constant that depends on a parameter of the receiving antenna,
$E_T(f)$ is the electromagnetic signal as a function of the frequency f, $E_R(f)$ is the modulated electromagnetic signal received by the receiving antenna as a function of the frequency f, $f_0 = \omega_0/2\pi$, and $f_1 = \omega_1/2\pi$.

6. The biological status evaluation system of claim 1, wherein the biological tissue is a human brain.

7. The biological status evaluation apparatus of claim 1, wherein the biological tissue is not in contact with the transmitting antenna or the receiving antenna while in the evaluation space.

8. A biological status evaluation system, comprising:
a signal generator configured to generate an electromagnetic signal at one or more frequencies;
a transmitting antenna including a transmitting antenna impedance and configured to transmit the electromagnetic signal;
a receiving antenna including a receiving antenna impedance and positioned relative to the transmitting antenna such that an evaluation space is defined between the transmitting antenna and the receiving antenna, wherein the evaluation space is configured to receive a biological tissue; and
a computing device configured to:
analyze a modulated electromagnetic signal after the transmitted electromagnetic signal propagates through the biological tissue,
calculate an evaluation parameter based on electrical properties of the biological tissue, wherein the modulated electromagnetic signal as compared to the transmitted electromagnetic signal is altered based on the electrical properties of the biological tissue, and is calculated by:

$$\Delta \equiv \int_{\omega_0}^{\omega_1} \left( \left( \frac{V_T^2(\omega)}{Z_T(\omega)} \right) - \left( \frac{V_R^2(\omega)}{Z_R(\omega)} \right) \right)$$

where:
$\Delta$ is the evaluation parameter,
$V_T$ is the voltage at the transmitting antenna,
$V_R$ is the voltage at the receiving antenna,
$Z_T(\omega)$ is the magnitude of the transmitting antenna impedance,
$Z_R(\omega)$ is the magnitude of the receiving antenna impedance,
$\omega_0$ is a lower bound of a sampled frequency spectrum, and
$\omega_1$ is an upper bound of the sampled frequency spectrum, and
generate a biological status indicator of the biological tissue based on the evaluation parameter.

9. The biological status evaluation system of claim 8, wherein the computing device is further configured to:
calculate the evaluation parameter based on an energy difference between the transmitted electromagnetic signal and the modulated electromagnetic signal, wherein the evaluation parameter is indicative of the electrical properties of the biological tissue.

10. The biological status evaluation system of claim 8, wherein the computing device is further configured to:
calculate the evaluation parameter based on a dielectric constant of the biological tissue, wherein the modulated electromagnetic signal as compared to the transmitted electromagnetic signal is altered based on the dielectric constant of the biological tissue.

11. The biological status evaluation system of claim 8, wherein the computing device is further configured to:
calculate the evaluation parameter based on a conductivity of the biological tissue, wherein the electromagnetic signal as compared to the transmitted electromagnetic signal is altered based on the conductivity of the biological tissue.

12. The biological status evaluation system of claim 8, wherein the transmitting antenna and the receiving antenna are identical such that:

$\alpha_T^2 Z_T(\omega) = \alpha_R^2 Z_R(\omega)$ and the evaluation parameter is calculated by:

$\Delta = \int_{f_0}^{f_1} df (|E_T(f)|^2 - |E_R(f)|^2)$, where:
$\alpha_T$ is a constant that depends on a parameter of the transmitting antenna,
$\alpha_R$ is a constant that depends on a parameter of the receiving antenna,
$E_T(f)$ is the electromagnetic signal as a function of the frequency f,
$E_R(f)$ is the modulated electromagnetic signal received by the receiving antenna as a function of the frequency f,
$f_0 = \omega_0/2\pi$, and
$f_1 = \omega_1/2\pi$.

13. The biological status evaluation system of claim 8, wherein the biological tissue is a human brain.

14. The biological status evaluation apparatus of claim 8, wherein the biological tissue is not in contact with the transmitting antenna or the receiving antenna while in the evaluation space.

15. A biological status evaluation system, comprising:
a signal generator configured to generate an electromagnetic signal at one or more frequencies;
a transmitting antenna including a transmitting antenna impedance and configured to transmit the electromagnetic signal;
a receiving antenna including a receiving antenna impedance and positioned relative to the transmitting antenna such that an evaluation space is defined by the transmitting antenna and the receiving antenna, and is configured to receive a biological tissue of a human brain; and
a computing device configured to:
analyze a modulated electromagnetic signal after the transmitted electromagnetic signal propagates through the biological tissue of the human brain,
calculate an evaluation parameter based on an energy difference between the transmitted electromagnetic signal and the modulated electromagnetic signal, wherein the evaluation parameter is indicative of electromagnetic absorption in the biological tissue of the human brain, and is calculated by:

$$\Delta \equiv \int_{\omega_0}^{\omega_1} \left( \left( \frac{V_T^2(\omega)}{Z_T(\omega)} \right) - \left( \frac{V_R^2(\omega)}{Z_R(\omega)} \right) \right)$$

where:
$\Delta$ is the evaluation parameter,
$V_T$ is the voltage at the transmitting antenna,
$V_R$ is the voltage at the receiving antenna,
$Z_T(\omega)$ is the magnitude of the transmitting antenna impedance, $Z_R(\omega)$ is the magnitude of the receiving antenna impedance, $\omega_0$ is a lower bound of a sampled frequency spectrum, and $\omega_1$ is an upper bound of the sampled frequency spectrum, and provide a biological status of the biological tissue of the human brain to a treating clinician for the treating clinician to evaluate treatment options of the biological tissue of the human brain.

16. The biological status evaluation apparatus of claim 15, wherein the computing device is further configured to:

determine the energy difference between the transmitted electromagnetic signal and the modulated electromagnetic signal by comparing a power measurement of the transmitted electromagnetic signal to a power measurement of the modulated electromagnetic signal; and calculate the evaluation parameter based on a power difference between the transmitted electromagnetic signal and the modulated electromagnetic signal.

17. The biological status evaluation system of claim 16, wherein the computing device is further configured to determine a cross-sectional area of a neurological event within the biological tissue based on the power difference between the transmitted electromagnetic signal and the modulated electromagnetic signal.

18. The biological status evaluation system of claim 15, wherein the transmitting antenna and the receiving antenna are identical such that:

$$\alpha_T^2 Z_T(\omega) = \alpha_R^2 Z_R(\omega)$$

and the evaluation parameter is calculated by:

$$\Delta = \int_{f_0}^{f_1} df (|E_T(f)|^2 - |E_R(f)|^2),$$

where:

$\alpha_T$ is a constant that depends on a parameter of the transmitting antenna, $\alpha_R$ is a constant that depends on a parameter of the receiving antenna, $E_T(f)$ is the electromagnetic signal as a function of the frequency f, $E_R(f)$ is the modulated electromagnetic signal received by the receiving antenna as a function of the frequency f, $f_0 = \omega_0/2\pi$, and $f_1 = \omega_1/2\pi$.

19. The biological status evaluation system of claim 15, wherein the computing device is further configured to generate an alert when the biological status of the biological tissue of the human brain requires treatment by the treating clinician to treat the biological tissue of the human brain.

20. The biological status evaluation system of claim 19, wherein the computing device is further configured to provide an updated biological status of the biological tissue of the human brain as the treating clinician provides treatment to the biological tissue of the human brain.

* * * * *

UNITED STATES PATENT AND TRADEMARK OFFICE
CERTIFICATE OF CORRECTION

PATENT NO. : 10,506,936 B2  
APPLICATION NO. : 15/174308  
DATED : December 17, 2019  
INVENTOR(S) : Joseph Floyd Clark et al.

Page 1 of 1

It is certified that error appears in the above-identified patent and that said Letters Patent is hereby corrected as shown below:

On the Title Page

At item (72) reads:
"Joseph Floyd Clark Cincinnati, OH (US); Matthew L. Flaherty Cincinnati, OH (US); George Shaw Cincinnati, OH (US); Opeolu Adeoye Cincinnati, OH (US)"

But should be:
"Joseph Floyd Clark Cincinnati, OH (US); Matthew L. Flaherty Cincinnati, OH (US); George Shaw Cincinnati, OH (US); Opeolu Adeoye Cincinnati, OH (US); Joseph J. Korfhagen, Cincinnati, OH (US)"

Signed and Sealed this  
Ninth Day of June, 2020

Andrei Iancu  
*Director of the United States Patent and Trademark Office*